US00PP09883P

United States Patent [19]

Zaiger et al.

[11] Patent Number: Plant 9,883

[45] Date of Patent: May 6, 1997

[54] PEACH TREE 'SPRING SNOW'

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 599,465

[22] Filed: Dec. 6, 1995

[51] Int. Cl.[6] ..... A01H 5/00

[52] U.S. Cl. ..... Plt./42.1

[58] Field of Search ..... Plt./42.1

*Primary Examiner*—James R. Feyrer

[57] ABSTRACT

A new and distinct variety of peach, *Prunus persica*, tree, its novelty consists of the following unique combination of desirable features:

1. Heavy and regular bearer of white flesh, clingstone fruit.
2. Fruit with very good flavor and eating quality.
3. Fruit with firm flesh, good storage and shipping quality.
4. Fruit having a high degree of attractive red skin color.
5. Early maturity of large size fruit.
6. Vigorous, upright growth.

1 Drawing Sheet

ORIGIN OF THE VARIETY

The present new and distinct variety of peach tree was originated by us in our experimental orchard located near Modesto, Calif., as a third generation cross between two selected seedlings, identification numbers 47EB280 and 1GC131. The maternal parent 47EB280 originated from a cross between two selected seedlings, 29G560 and 17G185. The selected seedling 29G560 originated from a cross of O'Henry Peach (U.S. Plant Pat. No. 2,964) with Giant Babcock Peach (U.S. Plant Pat. No. 1,353); and the selected seedling 17G185 originated from a cross of Fayette Peach (non-patented) with May Grand Nectarine (U.S. Plant Pat. No. 2,794). The paternal parent 1GC131 also originated from a cross between two selected seedlings, 41G1176 and 42G280.The selected seedling 41G1176 originated from an open pollinated peach seedling of unknown parentage and the selected seedling 42G280 originated from an open pollinated seedling selection of May Grand Nectarine (U.S. Plant Pat. No. 2,794). We grew and maintained a large group of these third generation seedlings under careful observation, during which time one such seedling, which represents the present variety, having especially desirable fruit characteristics, was selected for asexual reproduction and commercialization.

ASEXUAL REPRODUCTION OF THE VARIETY

The present new variety of peach tree was asexually propagated by budding, as performed by us in our experimental orchard located near Modesto, Calif. which shows that said characteristics of the tree and its fruit are established and transmitted through succeeding asexual propagation and comes true to the original tree in all respects.

SUMMARY OF THE VARIETY

The herein described variety of peach tree is of large size, vigorous, upright growth and a productive and regular bearer of large white flesh, clingstone fruit with very good flavor and eating quality. The fruit is further characterized by being relatively uniform in size throughout the tree, having an attractive red skin color, firm white flesh, with good handling and shipping qualities. The fruit ripens in the early maturity season, approximately one week before Sugar May Peach (U.S. Plant Pat. No. 8,034).

PHOTOGRAPH OF THE VARIETY

The accompanying color photograph shows a reproduction of the foliage and fruit of the new variety of peach tree. The illustration is of the upper and lower surface of the leaves; an exterior and sectional view of the fruit divided in the suture plane to reveal flesh coloration, pit cavity and a stone remaining in place.

DESCRIPTION OF THE VARIETY

The following is a detailed botanical description of the new and distinct variety of peach tree, its flowers, foliage and fruit as based on observations of the specimens grown in our experimental orchard located near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Bearer.*—Regular.
- *Production.*—Productive.

Trunk:
- *Size.*—Large.
- *Texture.*—Medium shaggy.
- *Color.*—Brown to grayish brown (6-D-5) to (6-E-5).

Branches:
- *Size.*—Medium.
- *Texture.*—Smooth to medium rough. Varies with age of growth.
- *Color.*—Light brown to brown.
- *Lenticels.*—Medium number. Medium size.

Leaves:
- *Size.*—Large. Average length—7'. Average width—1½'.
- *Form.*—Lanceolate. Pointed.
- *Margin.*—Crenate.
- *Petiole.*—Medium length. Medium thickness.
- *Surface.*—Smooth.
- *Glands.*—Reniform. Medium size. Number varies from 1 to 4. Average number 2. Located on upper portion of petiole and lower portion of leaf blade.

Flower buds:
- *Size.*—Large.
- *Form.*—Plump.

*Pubescence.*—Pubescent.

Flowers:

*Size.*—Large — showy.

*Blooming period.*—Mar. 3, 1994 to Mar. 8, 1994. Varies slightly with climatic conditions.

*Pollen.*—Present.

*Color.*—Pink.

Fruit:

*Maturity when described.*—Firm ripe.

*Date of first picking.*—May 26, 1994.

*Date of last picking.*—Jun. 1, 1994.

*Size.*—Large. Comparatively uniform. Average diameter axially 3'. Average transversely in suture plane 3⅛'.

*Form.*—Nearly globose — slightly flattened at stem end.

*Suture.*—Shallow — extends from base to apex.

*Ventral surface.*—Very shallow — nearly rounded.

*Base.*—Retuse.

*Cavity.*—Rounded to slightly elongated in suture plane. Average depth — ½'. Average breadth — 1'.

*Apex.*—Usually slight point, varies from rounded to slight point.

Flesh:

*Ripens.*—Evenly.

*Texture.*—Firm.

*Juice.*—Moderate.

*Fibers.*—Few, small, tender.

*Flavor.*—Very good, sub-acid, mild and sweet.

*Aroma.*—Moderate.

*Amygdalin.*—Undetected.

*Color.*—White to pinkish white (7-A-1) to (7-A-2). Pit cavity varies from white to yellowish white (1-A-1) to (1-A-2) with slight red extending into flesh, primarily toward apex.

Skin:

*Thickness.*—Medium.

*Texture.*—Medium tough; tenacious to the flesh.

*Down.*—Moderate, medium length.

*Tendency to crack.*—None.

*Color.*—White to yellowish white ground color (1-A-1) to (1-A-2). Nearly overspread with light red to madden red (10-A-7) to (10-B-7).

Stone:

*Type.*—Clingstone.

*Size.*—Large. Average length 1½'. Average breadth 1 1/16'. Average thickness ⅝'.

*Form.*—Oval to ovoid.

*Base.*—Varies from straight to rounded.

*Apex.*—Cuspidate — small to medium size.

*Sides.*—Equal to unequal.

*Surface.*—Irregularly furrowed toward apex, pitted toward base. Pits vary from round to slightly elongated. Ridges usually rounded.

*Tendency to split.*—Very slight.

*Color.*—Brown to reddish brown (9-E-5) to (9-D-4).

Use:

*Market.*—Local and long distance. Dessert.

Shipping quality: Good.

Keeping quality: Good.

The new and distinct peach tree, its flowers, foliage and fruit herein described may vary in slight detail due to climate, soil conditions and cultural practices under which the variety may be grown; the present description is that of the variety grown under the ecological conditions prevailing near Modesto, Calif.

We claim:

1. A new and distinct variety of peach tree, substantially as illustrated and described, characterized by its large size, vigorous upright growth, and being a productive and regular bearer of large, white flesh, clingstone fruit with very good flavor and eating quality; the fruit is further characterized by having firm flesh with good handling and shipping quality, having a high degree of attractive red skin color and ripening in the early maturity season, approximately one week before the white flesh Peach Sugar May (U.S. Plant Pat. No. 8,034).

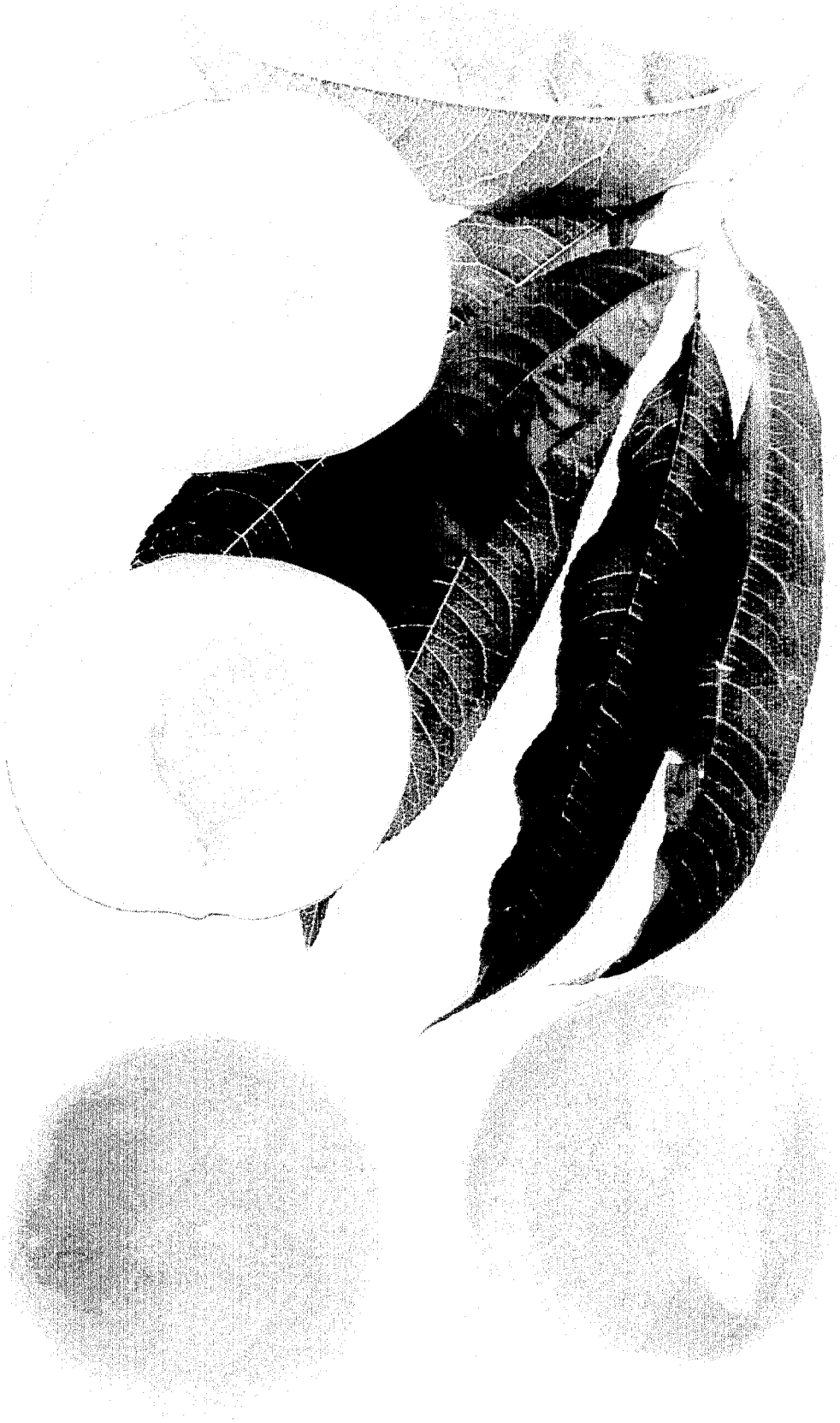

* * * * *